(12) United States Patent
Tatsumi et al.

(10) Patent No.: US 6,372,927 B2
(45) Date of Patent: Apr. 16, 2002

(54) PROCESS FOR PREPARING ALKYLENE OXIDE ADDUCTS

(75) Inventors: Nobuhiro Tatsumi; Yoshikazu Ogura; Takanobu Katayama; Osamu Tabata, all of Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/132,089

(22) Filed: Aug. 10, 1998

(30) Foreign Application Priority Data

Aug. 11, 1997 (JP) .............................................. 9-216593

(51) Int. Cl.$^7$ .............................................. C07C 51/00
(52) U.S. Cl. ...................... 554/149; 568/571; 568/583; 568/589; 568/606; 568/613; 568/616; 568/618
(58) Field of Search .......................... 554/149; 568/583, 568/584, 571, 606, 613, 616, 618

(56) References Cited

U.S. PATENT DOCUMENTS 4,727,199 A * 2/1988 King .......................... 568/620

FOREIGN PATENT DOCUMENTS

| DE | 1329160 | * | 1/1971 | ............. B01F/3/04 |
| DE | 2064356 | * | 11/1981 | ............ B01J/08/02 |
| DE | 196 11 508 | | 7/1997 | |
| EP | 0 421 677 | | 4/1991 | |
| GB | 2 035 306 | | 6/1980 | |
| GB | 2 064 356 | | 6/1981 | |
| GB | 44 46 064 | | 6/1995 | |

OTHER PUBLICATIONS

Fukushima et al, Interfacial area and boundary of hydrodynamic flow region in packed column with cocurrent downward flow Journal of Chemical Engineering Japan, vol. 10 No. 6, 1977.*
Derwent Abstracts, AN 88–031432, JP 7–002662, Jan. 18, 1995.
Derwent Abstracts, AN 80–31340C, JP 55–049332, Apr. 9, 1980.
Derwent Abstracts, AN 78–09141A, JP 52–151108, Dec. 15, 1977.
Derwent Abstracts, AN 88–031432, JP 62 289537, Dec. 16, 1987.
Derwent Abstracts, AN 78–09141, JP 52 151108, Dec. 15, 1977.
Derwent Abstracts, AN 78–35760, JP 53 037607, Apr. 6, 1978.

* cited by examiner

*Primary Examiner*—Deborah D. Carr
(74) *Attorney, Agent, or Firm*—Oblon, Spivak, McClelland, Maier & Neustadt, P.C.

(57) ABSTRACT

The process for preparing an alkylene oxide adduct, including the steps of feeding an organic compound having active hydrogen and an alkylene oxide to a reaction column packed with a solid catalyst, and carrying out addition reaction of the organic compound having active hydrogen with an alkylene oxide in a gas-liquid fixed bed reaction, wherein the alkylene oxide is in a state of gas and the organic compound having active hydrogen is in a state of liquid.

8 Claims, 3 Drawing Sheets

PROCESS FOR PREPARING ALKYLENE OXIDE ADDUCTS

BACKGROUND OF THE INVENTION

1. Field of the Invention

The present invention relates to a process for preparing an alkylene oxide adduct of an organic compound having active hydrogen.

2. Discussion of the Related Art

Alkylene oxide adducts have recently become increasingly significant in such applications as surfactants, starting materials for toner binders, and anti-foaming agents. In addition, since the development of their applications and improvement in performance are expected, a process for preparing such alkylene oxide adducts at low costs is in demand. The most important alkylene oxide adducts are those in which an alkylene oxide is added to an alcohol, a fatty acid, an aliphatic amine, an aliphatic amide, or a fatty acid ester, the resulting alkylene oxide adduct constituting a very important group of nonionic surfactants.

The above alkylene oxide adduct may be prepared, for instance, by contacting the alkylene oxide with the organic compound having active hydrogen by a process comprising spraying an alkylene oxide to an organic compound having active hydrogen, or alternatively spraying an organic compound having active hydrogen to a reactor filled with an alkylene oxide; and carrying out addition reaction therebetween. In both cases, the alkylene oxide is added in accordance with the progress of the reaction process (semi-batch operation), and the reaction mixture in a state of liquid is stirred until a point where a desired amount of an alkylene oxide is reacted.

In addition, Japanese Patent Laid-Open No. Sho 55-49332 discloses a process for preparing an alkylene glycol monoether by using a fixed bed apparatus in which clay having a Montmorillonite structure exchanged with a particular cation is used as a solid catalyst.

This process has the following advantages:
1) An alkylene glycol monoether can be prepared in a high yield from an alcohol and an alkylene oxide; and
2) Since a solid catalyst is used, steps, such as separation of a catalyst and after-treatments, can be omitted.

However, since the process is involved with a liquid—liquid fixed bed reaction in which an organic compound having active hydrogen and an alkylene oxide are reacted in a state of liquid, the addition reaction dramatically proceeds at an inlet of the reactor. Therefore, in certain cases, there arise, for instance, the following problems:
1) A drastic temperature rise owing to the exothermic reaction by the addition of the alkylene oxide takes place, thereby resulting in an increase in pressure; and
2) Higher the proportion of the alkylene oxide to the alcohol, larger the amount of exothermic heat, so that the quality deterioration is likely to take place.

In addition, Japanese Examined Patent Publication No. Hei 7-2662 gives examples of a liquid-liquid fixed bed reactor using a similar catalyst as above. However, it is required that a large amount of a liquid is circulated, and that the amount of molar additions of the alkylene oxide is relatively controlled to a low level in order to suppress the exothermic heat and pressure increase upon reaction. In other words, in order to suppress exothermic heat and pressure increase, the amount of molar additions of the alkylene oxide should be relatively controlled to a low level, thereby consequently making it practically impossible to prepare an alkylene oxide adduct having a large number of molar additions. In order to prepare an alkylene oxide adduct having a large number of molar additions, the resulting reaction mixture can be circulated and reacted. However, in such cases, the production efficiency can be notably lowered.

In the addition reaction of the alkylene oxide by employing a fixed bed reactor, there have not been found an example where the number of molar additions is larger than those of these examples. This is because heat generated at an initial stage of reaction and pressure increase owing to the exothermic heat would be difficult to be overcome.

Japanese Patent Laid-Open No. Sho 52-151108 discloses an addition reaction of ethylene oxide using a conventional homogeneous base catalyst in a tube-type reactor having a mode of reaction similar to that of the liquid—liquid fixed bed reaction. This method is involved with a liquid—liquid homogeneous reaction, not a fixed bed reaction, the method having a mode of reaction similar to that of the liquid—liquid fixed bed reaction. This publication shows in its comparative examples that it is difficult to increase the number of molar additions of the alkylene oxide.

In Comparative Example 1 of the publication, it is disclosed that a higher alcohol having an average molecular weight of 208 adjusted to 170° C. is fed to a reaction column having an inner diameter of 9.4 mm and a length of 25 m at a flow rate of 3.75 kg/hr, and ethylene oxide is fed from an inlet of the reaction column at a flow rate of 2.4 kg/hr. Under the above conditions, the highest temperature at 1.8 m from the inlet of the reaction column is 400° C. or more, and the pressure is 100 kg/cm$^2$·G or more, so that further continuation of the reaction becomes difficult, thereby making the resulting product to have brownish coloring and an extremely viscous state, impractical for actual use.

From the above results, in case of preparing by a liquid—liquid fixed bed reaction, an alkylene oxide adduct having the same level of a number of molar additions, i.e. 3 molar addition, as this comparative example, there can be easily deduced very high levels of exothermic heat at an inlet of the reaction column and a pressure increase caused thereby.

Accordingly, an object of the present invention is to provide a process for preparing an alkylene oxide adduct having excellent production efficiency without necessitating a high-level, pressure-withstanding equipment.

Another object of the present invention is to provide a process for preparing an alkylene oxide adduct with easy reaction control, thereby consequently making it possible to operate safely and stably by using a simple equipment.

These and other objects of the present invention will be apparent from the following description.

SUMMARY OF THE INVENTION

The present inventors have carried out addition reaction by a gas-liquid fixed bed reaction using a reaction column packed with a solid catalyst, and confirmed that improvements in production efficiency in a high-concentration catalyst reaction. They have found that by reacting an alkylene oxide in the state of a gas, the alkylene oxide concentration in the liquid can be made relatively uniform in the reaction column, so that no drastic exothermic heat and pressure increase incurred by the exothermic heat take place. Therefore, the gas-liquid fixed bed reaction can be operated safely and stably, and the present invention has been perfected thereby. Further, the present inventors have confirmed that in the preparation according to the conventional processes, when the number of molar additions of the alkylene oxide is high, the quality deterioration takes place owing to the reaction temperature rise by the exothermic heat, whereas in the process of the present invention, unexpectedly no quality deterioration of the resulting alkylene oxide adduct has been found.

The present invention pertains to a process for preparing an alkylene oxide adduct, comprising the steps of feeding an organic compound having active hydrogen and an alkylene oxide to a reaction column packed with a solid catalyst, and carrying out addition reaction of the organic compound having active hydrogen with an alkylene oxide in a gas-liquid fixed bed reaction, wherein the alkylene oxide is in a state of gas and the organic compound having active hydrogen is in a state of liquid.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein.

DETAILED DESCRIPTION OF THE INVENTION

The organic compound having active hydrogen usable in the present invention is not particularly limited. Examples thereof include alcohols, fatty acids, amines, amides, esters, admixtures thereof, and the like.

Examples of the alcohols include fatty alcohols each having 6 to 22 carbon atoms; linear or branched, synthetic alcohols each having 1 to 20 carbon atoms; phenols, such as nonyl phenol, tribenzyl phenol, styrenated phenol, paraoctyl phenol, and the like; monoglyceride, diglyceride, glycerol, ethylene glycol, and the like. Examples of the fatty acids include saturated or unsaturated fatty acids having 6 to 22 carbon atoms. Examples of the amines include primary amines, such as coconut amine, octylamine, laurylamine, myristylamine, stearylamine, oleylamine, and tallow amine; secondary amines, such as distearylamine; and tertiary amines, such as dimethyl coconut amine, dimethyl octylamine, dimethyl decylamine, dimethyl laurylamine, dimethyl myristylamine, dimethyl palmitylamine, dimethyl stearylamine, dilauryl monomethylamine, and trioctylamine. Examples of the amides include alkyl alkanolamides, and the like. Examples of the esters include fatty acid esters of monohydric alcohols, such as lower alcohols, fatty alcohols, and phenols; and fatty acid esters of polyhydric alcohols, such as ethylene glycol and glycerol.

Examples of the alkylene oxide include lower alkylene oxides, such as ethylene oxide, propylene oxide, and butylene oxide. Those alkylene oxides may be used alone or in an admixture thereof.

In addition, these alkylene oxides may be used together with an inert gas, which is not particularly limited as long as it does not hinder the addition reaction of the alkylene oxide. Concrete examples thereof include nitrogen gas, helium gas, neon gas, argon gas, and the like. Those inert gases may be used alone or in an admixture thereof.

Examples of the solid catalyst usable in the present invention include compounds of alkaline earth metal elements, such as compounds of barium, strontium, and calcium, including, for instance, barium phosphate compound ($Ba_3(PO_4)_2$); complexes formed between an antimony pentahalide, including antimony pentabromide, antimony pentachloride, or the like, and a Lewis base; an aluminum compound supported by a gel carrier, the aluminum compound being represented by the general formula (1):

wherein X is fluorine atom; and each of $R^1$ and $R^2$ is hydrogen atom, an alkyl group having 1 to 20 carbon atoms, or a halogen atom, with proviso that at least one of $R^1$ and $R^2$ is an alkyl group, and exemplified by dialkylaluminum fluorides and alkylaluminum difluorides; complex salts prepared by adding to magnesium oxide one or more metal ions selected from the group consisting of $Al^{3+}$, $Ga^{3+}$, $In^{3+}$, $Tl^{3+}$, $Co^{3+}$, $Se^{3+}$, $La^{3+}$, $Mn^{2+}$, $Ba^{2+}$, $Si^{4+}$, $Cs^+$, $B^{3+}$, $Fe^{3+}$, $y^{3+}$, and $Ce^{3+}$ by impregnation method or coprecipitation method; Al-Mg compound oxides represented by the general formula (2):

$$nMgO \cdot Al_2O_3 \cdot mH_2O, \qquad (2)$$

wherein each of n and m is a positive number, the compound oxides being prepared by baking and activating a composite hydroxide of aluminum-magnesium; hydrotalcite; calcinated hydrotalcite; zirconium oxysulfate; and composites of a calcium salt, an aluminum trialkoxide, and an inorganic acid; calcinated hydrotalcite group (for instance, a molded product of "KW 2000," manufactured by Kyowa Chemical Industry Co., Ltd. can be used as a generally commercially available catalyst); molded products of catalysts disclosed in Japanese Patent Laid-Open No. Hei 8-323200; molded catalysts made of MgO, CaO, BaO, ZnO, and the like.

The reaction column usable in the present invention is one packed with a solid catalyst, which serves as a reaction field for the fixed bed reaction. The size of the reaction column is not particularly limited, and a size which can cool to an extent not to cause quality deterioration of the alkylene oxide adduct owing to the exothermic heat resulting from the reaction can be appropriately selected. The inner diameter is preferably from 9 mm to 2 m, more preferably from 15 mm to 1 m, still more preferably from 20 mm to 500 mm. From the viewpoint of uniformly wetting the catalyst, the inner diameter is preferably 9 mm or more, and from the viewpoints of thermal removability and equipment costs, the inner diameter is preferably 2 m or less. In addition, the length is preferably from 0.5 to 12 m, more preferably from 1 to 10 m, still more preferably from 1 to 8 m. From the viewpoint of productivity, the length is preferably 0.5 m or more, and from the viewpoints of operational conditions such as pressure loss, the length is preferably 12 m or less.

In addition, in the process of the present invention, since the pressure rise upon the reaction can be suppressed, the reaction column can be desirably designed to withstand a pressure of about 30 atm, preferably about 20 atm, more preferably about 15 atm, so that it is not necessitated that the reaction column is designed to have a thick wall for the reaction column as in the case of the reaction column for carrying out conventional liquid—liquid reaction.

In addition, substances comprising inert particles which do not participate in the addition reaction may be provided at a lower portion of the solid catalyst to fix the solid catalyst inside the reaction column, or the above substances may be provided at an upper portion of the solid catalyst, so that the liquid phase and the gas phase introduced to the solid catalyst can be prevented from becoming ununiformed. The inert particles include packings such as Raschig rings, McMahon packings, spheres made of ceramic, iron or stainless.

Also, in the present invention, a multi-column type reactor comprising a plurality of reaction columns may be used.

The modes for carrying out the gas-liquid fixed bed reaction in the present invention include, for instance, gas-liquid, cocurrent, downward flow fixed beds; gas-liquid, countercurrent fixed beds; gas-liquid, cocurrent, upward flow fixed beds, and the like.

The organic compound having active hydrogen, the alkylene oxide, and the inert gas are fed to the reaction column, for instance, in the following manner. Here, in a case where an inert gas is not used, the gas phase is constituted by the alkylene oxide. In this case, it is not necessitated that the alkylene oxide is fed to the reaction column in a state of gas, and the alkylene oxide may be fed in a state of liquid, as long as a part or entire alkylene oxide is gasified in the reaction column.

Also, in the case where the gas-liquid fixed bed reaction is carried out under conditions that the gas phase is a continuous phase (hereinafter simply referred to as "Embodiment-1"), an embodiment include, for instance, a process comprising previously feeding an inert gas to the reaction column to form a continuous phase of the gas, and thereafter feeding a liquid organic compound having active hydrogen and a liquid or gaseous alkylene oxide to the reaction column.

Alternatively, in the case where the gas-liquid fixed bed reaction is carried out under conditions that the liquid phase is a continuous phase (hereinafter simply referred to as "Embodiment-2"), an embodiment includes, for instance, a process comprising previously feeding a liquid organic compound having active hydrogen to the reaction column in an upward direction, and subsequently feeding an inert gas and a liquid or gaseous alkylene oxide to the reaction column in the upward direction.

The flows of the liquid phase and the gas phase inside the reaction column are preferably in a cocurrent, downward flow, from the viewpoint of constituting a continuous phase of the gas phase and widening operability.

The flow rate of the organic compound having active hydrogen to the reaction column is not particularly limited. Although the flow rate may be changed by the desired number of molar additions of the alkylene oxide to the organic compound having active hydrogen or catalytic activity, the flow rate is adjusted such that the particle-based Reynolds number of the liquid inside the reaction column is preferably 1000 or less, more preferably 500 or less, particularly 200 or less. Incidentally, the Reynolds number of the liquid should be theoretically calculated in consideration of the alkylene oxide in a state of liquid as well as the organic compound having active hydrogen. However, since most of the alkylene oxide are actually gasified, practically speaking, there would be no problem if the Reynolds number of the organic compound having active hydrogen is assumed to be the Reynolds number of the liquid.

In addition, the flow rate of the alkylene oxide to the reaction column is not particularly limited. Incidentally, in order to efficiently prepare a desired alkylene oxide adduct of the present invention having a large number of molar additions, the molar ratio of the alkylene oxide to the organic compound having active hydrogen is preferably 1.1 times or more of the desired number of molar additions, more preferably 1.3 times or more, still more preferably 1.5 times or more.

In the case where an inert gas is used, the feed amount of the inert gas to the reaction column is not particularly limited. Concretely, it is preferred that the particle-based Reynolds number of a gas in the reaction column is 300,000 or less, more preferably 100,000 or less, particularly 50,000 or less. In the case where ethylene oxide is used as an alkylene oxide, it is preferred that the inert gas is fed in a manner such that the concentration of ethylene oxide in the gas phase is outside the explosion limit.

The pressure of the reaction column is not particularly limited, and it may be of a known level generally employed in the art. Concretely, the pressure is preferably from 1 to 30 atm, more preferably from 2 to 20 atm, and still more preferably from 2 to 15 atm. From the viewpoint of productivity, the pressure is preferably 1 atm or more, and from the viewpoint of equipment costs, the pressure is preferably 30 atm or less.

As to the reaction temperature, it varies depending upon the catalytic activities, and the like. Any reaction temperature can be appropriately chosen in a range in which the addition reaction smoothly proceeds and no quality deterioration of the resulting alkylene oxide adduct takes place. A generally employed, known temperature range can be used. For instance, the temperature range of 20° to 300° C. is preferred, more preferably 30° to 250° C., still more preferably 40° to 230° C. From the viewpoint of reactivity, the preferred reaction temperature is 20° C. or more, and from the viewpoint of preventing quality deterioration, the preferred reaction temperature is 300° C. or less.

The resulting alkylene oxide adduct is included in the liquid components, reaching a liquid outlet of the reaction column. The reaction column may further comprise a gas-liquid separator for efficiently separating the gas components and the liquid components at a liquid outlet of the reaction column. In the gas-liquid separator, the gas components are separated from the liquid components containing the alkylene oxide adduct and unreacted starting materials. The separated liquid components can be easily divided into the alkylene oxide adduct and the unreacted starting materials by a conventionally known purification means. Incidentally, in a case where the liquid phase is in an upward flow, the top of the reaction column is a liquid outlet of the reaction column, and the bottom of the reaction column is a liquid inlet of the reaction column. On the other hand, when the liquid phase is in a downward flow, the top of the reaction column is a liquid inlet of the reaction column, and the bottom of the reaction column is a liquid outlet of the reaction column.

In addition, in the present invention, the process of preparation of the alkylene oxide adduct may be carried out in a closed-system without exhausting the feeding gas components to outside the reaction system, or the process may be carried out in an open-system where the feeding gas components are exhausted to outside the reaction system.

In a case where the process of the present invention is carried out in a closed-system, an embodiment includes a process comprising circulating and reusing gas components, namely an unreacted alkylene oxide gas or a mixed gas of the unreacted alkylene oxide gas and an inert gas, without exhausting from the closed-system. By circulating and reusing the gas components, the serviceable efficiency of the inert gas and the alkylene oxide can be notably improved, and the amount of the alkylene oxide exhausted to the atmosphere can be notably reduced. Concretely, circulation and reuse of the gas components can be achieved by connecting a portion accumulating the gas components at a gas outlet of a reaction column, for instance, an upper portion of a gas-liquid separator, to a gas inlet of the reaction column by means of a lead pipe. In order to circulate more effectively, a pump, a blower, an ejector for liquid starting materials, or the like may be employed. Incidentally, when the gas phase is in an upward flow, the top of the reaction column is a gas outlet of the reaction column, and the bottom of the reaction column is a gas inlet of the reaction column. On the other hand, when the gas phase is in a downward flow, the top of the reaction column is a gas inlet of the reaction column, and the bottom of the reaction column is a gas outlet of the reaction column.

In the case where circulation is carried out, the alkylene oxide may be fed in an amount to make up for consumption in the addition reaction and for discharge from the reaction column as a component dissolved in the liquid components. The inert gas may only be fed in an amount lost by the amount discharged as a component dissolved in the liquid components. Therefore, the serviceable efficiency of the starting materials, and the like can be improved. Moreover, the pressure and reactivity inside the reaction column can be kept at given levels, so that the operation can be safely carried out.

In a case where the process of the present invention is carried out in the open-system mentioned above, the gas components are exhausted from the gas outlet of the reaction column.

In addition, the number of molar additions of the alkylene oxide of the alkylene oxide adduct in the present invention can be easily adjusted to a desired level from the aspects of designs of the reactor, including, for instance, a catalyst volume inside the reaction column, a number of reaction columns when employing a multi-column type reactor, and the like; or from the aspects of individual reaction conditions, including, for instance, adjustment of the feeding rate of a feeding organic compound having active hydrogen, or adjustment of the amount of an alkylene oxide dissolved in the liquid phase by controlling the feeding rate of a feeding alkylene oxide, or the pressure inside the reaction column.

The reaction modes in the addition reaction of the present invention are not particularly limited, as long as a gas-liquid fixed bed reaction is carried out wherein the alkylene oxide is in a state of gas and the organic compound having active hydrogen is in a state of liquid in the reaction column. Examples of such reaction modes include Embodiment-1 and Embodiment-2 described above.

First, Embodiment-1 will be described.

In Embodiment-1, in the reaction column, an organic compound having active hydrogen, being in a downward flow or in an upward flow on the surfaces of packed catalyst, contacts an alkylene oxide which is present in a gas phase, to thereby cause addition reaction of the organic compound having active hydrogen with the alkylene oxide. The modes for Embodiment-1 include, for instance, gas-liquid, cocurrent, downward flow fixed beds; gas-liquid, counter-current fixed beds wherein the liquid phase is in a downward flow and the gas phase is in an upward flow; gas-liquid, cocurrent, upward flow fixed beds, and the like.

By carrying out the addition reaction under conditions that the gas phase is a continuous phase, the following advantages can be achieved:

a) The concentration of the alkylene oxide in the liquid components can be made substantially uniform in the entire reaction column, so that the reaction proceeds uniformly over the entire reaction column, thereby making the reaction milder than a liquid—liquid reaction, so that designing of a reaction column to have a high-level, pressure-withstanding equipment is not necessitated.

b) The extent of a temperature rise is suppressed, thereby resulting in excellent quality in such properties as hue of the resulting alkylene oxide adduct.

Here, the phrase "gas phase is a continuous phase" means that the gas phase is in a state of being continuously present in the reaction column from the gas inlet to the gas outlet of the reaction column. In the present invention, concrete embodiments of the gas phase are as follows:

i) A gas phase consisting essentially of an alkylene oxide gas, and ii) A gas phase comprising an inert gas and an alkylene oxide gas.

The alkylene oxide may be fed in a state of liquid, or it may be fed in a state of gas, including a case where the alkylene oxide is fed together with an inert gas. The alkylene oxide may be gasified in the reaction column in an amount corresponding to its vapor pressure, and the remaining alkylene oxide may be present in a state of liquid.

When the gasification ratio is defined as a proportion of the alkylene oxide gasified in the reaction column to the amount of the entire alkylene oxide fed to the reaction column, the extent of gasification of the alkylene oxide, i.e. the gasification ratio, is not particularly limited. The gasification ratio greatly varies depending upon the catalytic activities and the thermal removability of the reactor and thus cannot be generalized. Under conditions that the gas phase is a continuous phase in the reaction column, for instance, the gasification ratio is preferably 0.4 or more, more preferably 0.6 or more, still more 0.7 or more. In order to carry out a gas-liquid reaction by gasifying the alkylene oxide and to carry out the reaction uniformly over the entire reaction column, the gasification ratio is preferably 0.4 or more. The above gasification ratio can be adjusted to a desired level by properly adjusting the pressure inside the reaction column, the amount of the feeding alkylene oxide, the temperature inside the reaction column, and the like. The gasification ratio can be deduced from, for instance, calculation of a gas-liquid equilibrium using vapor pressures of the alkylene oxide and the organic compound having active hydrogen.

In the case where the reaction is carried out under conditions that the gas phase is a continuous phase, gas components comprising an alkylene oxide gas and/or an inert gas, and liquid components comprising an organic compound having active hydrogen, and in certain cases, further comprising an alkylene oxide, are preferably fed to the reaction column, feeding the gas components and the liquid components so as to satisfy a wavy flow region, which is defined as a flow region in which surfaces of a thin film in a downward flow in a wavy manner while forming a thin film with a liquid on solid catalyst surfaces, or to satisfy a trickle flow region, which is defined as a flow region in which surfaces of a thin film in a smooth downward flow while forming a thin film with a liquid on solid catalyst surfaces, the wavy flow region and the trickle flow region being disclosed in "JOURNAL OF CHEMICAL ENGINEERING OF JAPAN," FUKUSHIMA, S. et al., 10, No. 6, 461–467. In order to cause downward flow satisfying the above flow regions, the gas phase and the liquid phase are preferably fed in accordance with the following conditions.

Specifically, the wavy flow region or the trickle flow region can be defined as follows, referring to each of the graphs (FIGS. 1 and 2) showing the relationship between $Re_1$, the particle-based Reynolds number of a liquid, and $Re_g$, the particle-based Reynolds number of a gas. These flow regions are a region bound by line (I), line (II), line (III), ordinate, and abscissa of the graph in FIG. 1, namely region (a), region (b), and region (c); or a region bound by line (I), line (II), line (III), ordinate, and abscissa of the graph in FIG. 2, namely region (d), region (e), and region (f). It is more preferred in the present invention that the gas components and the liquid components are fed so that both $Re_g$ of the feeding gas components and $Re_1$ of the feeding liquid components satisfy the conditions in the above region.

Figure 1:
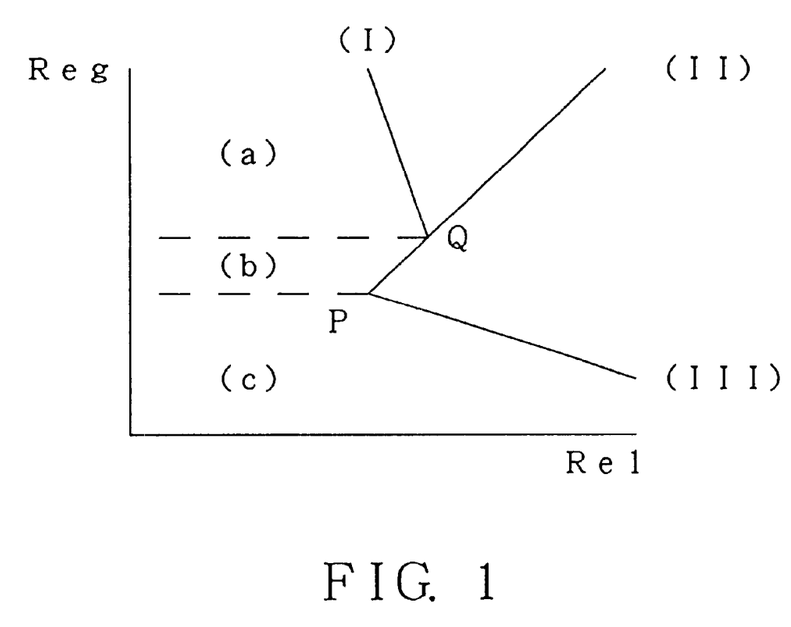
FIG. 1 is a graph showing the relationship between $Re_l$, the particle-based Reynolds number of a liquid, and $Re_g$, the particle-based Reynolds number of a gas.
Figure 2:
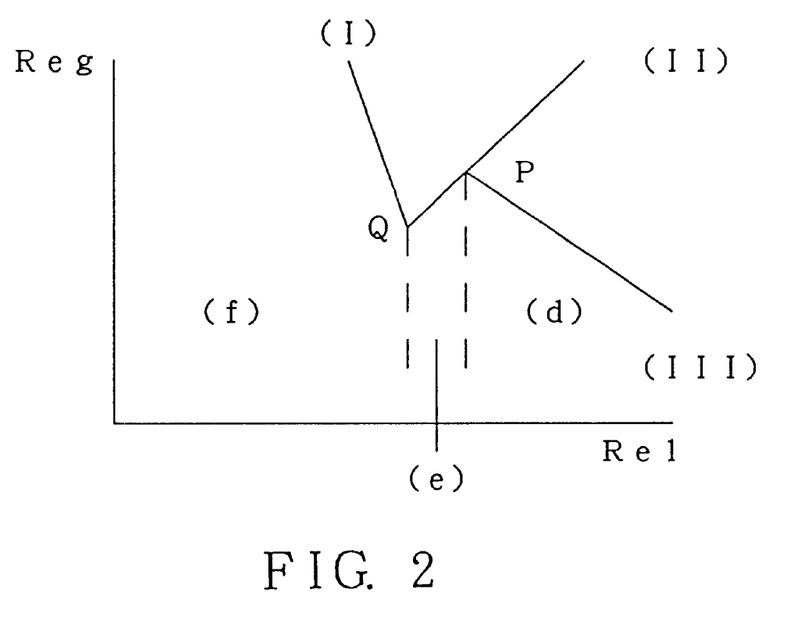
FIG. 2 is a graph showing the relationship between $Re_l$, the particle-based Reynolds number of a liquid, and $Re_g$, the particle-based Reynolds number of a gas.

In FIGS. 1 and 2, line (I) satisfies the following equation:

$$10 = Re_l^{0.45} \cdot Re_g^{0.13} \qquad \text{Eqn (I)}$$

Line (II) satisfies the following equation:

$$0.34 = \phi^{-0.1} \cdot Re_l^{0.52} \cdot Re_g^{-0.47} \qquad \text{Eqn (II)}$$

Line (III) satisfies the following equation:

$$18 = \phi^{-0.2} \cdot Re_l^{0.27} \cdot Re_g^{0.2} \cdot (d_p/T)^{-0.5} \qquad \text{Eqn (III)}$$

From Equations (I) to (III), an intersection P of line (II) and line (III), and an intersection Q of line (I) and (II) are calculated.

FIG. 1 is a graph showing a case where $Re_g$ at Point P is smaller than $Re_g$ at Point Q.

When $Re_g$ of the feeding gas components is greater than $Re_g$ at Point Q, the liquid components are preferably fed so as to have $Re_1$ of the feeding liquid components to be existing in the left side region of the boundary shown by line (I), namely within region (a). In other words, the liquid components are preferably fed such that $Re_l$ of the feeding liquid components satisfies the following (A):

$$Re_l \leq [10/(Re_g^{0.13})]^{1/0.45} \qquad (A)$$

When $Re_g$ of the feeding gas components is less than $Re_g$ at Point Q and greater than $Re_g$ at Point P, the liquid components are preferably fed so as to have $Re_l$ of the feeding liquid components to be existing in the left side region of the boundary shown by line (II), namely within region (b). In other words, the liquid components are preferably fed such that $Re_l$ of the feeding liquid components satisfies the following (B):

$$Re_l \leq [0.34/((\phi^{-0.1}) \cdot (Re_g^{-0.47}))]^{1/0.52} \qquad (B)$$

When $Re_g$ of the feeding gas components is less than $Re_g$ at Point P, the liquid components are preferably fed so as to have $Re_l$ of the feeding liquid components to be existing in the lower side region of the boundary shown by line (III), namely within region (c). In other words, the liquid components are preferably fed such that $Re_l$ of the feeding liquid components satisfies the following (C):

$$Re_l \leq [18/[(\phi^{-0.2}) \cdot (Re_g^{0.2}) \cdot ((d_p/T)^{-0.5})]]^{1/0.27} \qquad (C)$$

FIG. 2 is a graph showing a case where $Re_g$ at Point P is greater than or equal to $Re_g$ at Point Q.

When $Re_l$ of the feeding liquid components is greater than $Re_l$ at Point P, the gas components are preferably fed so as to have $Re_g$ of the feeding gas components to be existing in the lower side region of the boundary shown by line (III), namely within region (d). In other words, the gas components are preferably fed such that $Re_g$ of the feeding gas components satisfies the following (D):

$$Re_g \leq [18/[(\phi^{-0.2}) \cdot (Re_l^{0.27}) \cdot ((d_p/T)^{-0.5})]]^{1/0.2} \qquad (D)$$

When $Re_l$ of the feeding liquid components is less than $Re_l$ at Point P and greater than $Re_l$ at Point Q, the gas components are preferably fed so as to have $Re_g$ of the feeding gas components to be existing in the lower side region of the boundary shown by line (II), namely within region (e). In other words, the gas components are preferably fed such that $Re_g$ of the feeding gas components satisfies the following (E):

$$Re_g \leq [0.34/((\phi^{-0.1}) \cdot (Re_l^{0.52}))]^{(-1/0.47)} \qquad (E)$$

When $Re_l$ of the feeding liquid components is less than $Re_l$ at Point Q, the gas components are preferably fed so as to have $Re_g$ of the feeding gas components to be existing in the left side region of the boundary shown by line (I), namely within region (f). In other words, the gas components are preferably fed such that $Re_g$ of the feeding gas components satisfies the following (F):

$$Re_g \leq [10/(Re_l^{0.45})]^{1/0.13} \qquad (F)$$

Here, $Re_l$, the particle-based Reynolds number for the liquid components, is calculated by the following equation:

$$Re_l = d_s \cdot G_l/\mu_l,$$

wherein $d_s$ is an equivalent packing (catalyst) diameter based on sphere [cm]; $G_l$ is a superficial mass flow rate of a liquid [g/cm²·sec]; and $\mu_l$ is a viscosity of a liquid [g/cm·sec].

In addition, $Re_g$, the particle-based Reynolds number for the gas components, is calculated by the following equation:

$$Re_g = d_s \cdot G_g/\mu_g,$$

wherein $d_s$ is the same as defined above [cm]; $G_g$ is a superficial mass flow rate of a gas [g/cm²·sec]; and $\mu_g$ is a viscosity of a gas [g/cm·sec].

Further, $\phi$, the surface shape factor of packing (catalyst), is calculated by the following equation:

$$\phi = S/d_p^2,$$

wherein S is a geometrical surface of a packing (catalyst) [cm²]; and $d_p$ is a packing diameter [cm].

Moreover, the inner diameter of the reaction column is T [cm].

Next, Embodiment-2 will be described.

In Embodiment-2, an addition reaction of an organic compound having active hydrogen with an alkylene oxide is carried out by bringing the organic compound having active hydrogen in an upward flow in the reaction column packed with a catalyst in contact with the alkylene oxide dispersed in the liquid phase.

By carrying out the addition reaction under conditions that the liquid phase is a continuous phase, the following advantages can be achieved:

a) The concentration of the alkylene oxide in the liquid components can be made substantially uniform in the entire reaction column, so that the reaction proceeds uniformly over the entire reaction column, thereby making the reaction milder than a liquid—liquid reaction, so that designing of a reaction column to have a high-level, pressure-withstanding equipment is not necessitated.

b) The extent of a temperature rise is suppressed, thereby resulting in excellent quality in such properties as hue of the resulting alkylene oxide adduct.

Here, the phrase "liquid phase is a continuous phase" means that the liquid phase is in a state of being continuously present in the reaction column from the liquid inlet to the liquid outlet of the reaction column. In the present invention, concrete embodiments of the liquid phase are as follows:

i) A liquid phase comprising an organic compound having active hydrogen, and a partially liquefied and dissolved alkylene oxide; and ii) A liquid phase comprising an organic compound having active hydrogen, an alkylene oxide adduct of an organic compound having active hydrogen, and a partially liquefied and dissolved alkylene oxide.

The alkylene oxide may be fed in a state of liquid, or it may be fed in a state of gas, including a case where the alkylene oxide is fed together with an inert gas. The alkylene oxide may be gasified in the reaction column in an amount corresponding to its vapor pressure, and the remaining alkylene oxide may be present in a state of liquid.

The gasification ratio of the alkylene oxide in Embodiment-2 is not particularly limited. The gasification ratio greatly varies depending upon the catalytic activities and the thermal removability of the reactor and thus cannot be generalized. From the aspect of carrying out reaction uniformly over the entire reaction column, the gasification ratio is preferably 0.4 or more, more preferably 0.6 or more, still more preferably 0.7 or more.

By carrying out the addition reaction in the manner of Embodiment-1, Embodiment-2, and like as described above, the addition reaction can be carried out by a gas-liquid fixed bed reaction. From the viewpoint of operability and simplification in design of the reactor, Embodiment-1 is preferable. More preferably among Embodiment-1, the cocurrent, downward flow, wherein the liquid phase and the gas phase are both in a downward flow, is employed from the viewpoint of constituting a continuous phase of the gas phase and widening operability.

In addition, it is more preferred that the liquid components containing the resulting alkylene oxide adduct is further subjected to an aging treatment. By aging the resulting liquid components, the alkylene oxide dissolved in the liquid components can be further added to the alkylene oxide adduct or to the unreacted organic compound having active hydrogen. The aging can be carried out by further subjecting the liquid components to an aging treatment, including, for instance, a process comprising leading liquid components separated at a liquid outlet of the reaction column to an aging reaction column packed with a solid catalyst similar to that used for the above reaction column, and carrying out addition reaction of a dissolved unreacted alkylene oxide with the alkylene oxide adduct or with the unreacted organic compound having active hydrogen in the aging reaction column.

By employing the aging process described above, since the addition reaction takes place in the liquid components, the remaining alkylene oxide can be efficiently reacted and consumed in the reaction system, without affecting the gas-liquid equilibrium of the alkylene oxide, unlike the case of the conventional, semi-batch type aging process after the reaction.

The shape of the aging reaction column is not particularly limited. From the viewpoints of preventing back mixing of liquids and plug flow, tubular shaped ones are preferred. The size of the aging reaction column may vary depending upon the catalytic activities and the aging conditions such as aging temperature. For instance, those having an inner diameter of 9 to 1500 mm are preferable, more preferably those having an inner diameter of 15 to 1200 mm, still more preferably those having an inner diameter of 20 to 800 mm. From the viewpoint of pressure drop, those having an inner diameter of 9 mm or more are preferable. From the viewpoints of preventing back mixing of liquids and plug flow, those having an inner diameter of 1500 mm or less are preferable. The length of the aging reaction column is preferably 10 to 1000 cm, more preferably 40 to 900 cm, still more preferably 50 to 800 cm, still more preferably 100 to 700 cm. From the viewpoint of preventing back mixing of liquids and plug flow, those having a length of 10 cm or more are preferable, and from the viewpoint of pressure loss, those having a length of 1000 cm or less are preferable.

The velocity of the liquid components containing the alkylene oxide adduct to the aging reaction column is not particularly limited. Although the velocity varies depending upon the activities of the packed catalyst, the velocity in terms of LHSV (Liquid Hourly Space Velocity) is preferably from 0.1 to 100, more preferably from 0.2 to 70, still more preferably from 1 to 50. From the viewpoint of reducing equipment costs, the LHSV is preferably 0.1 or more, and from the viewpoint of sufficiently carrying out aging reaction of the unreacted alkylene oxide, the LHSV is preferably 100 or less.

In addition, as to the aging temperature and pressure, substantially the same level or lower temperature and/or substantially the level or higher pressure as compared to the temperature and pressure conditions at the gas-liquid separator in the bottom of the reaction column can be employed, whereby the dissolved alkylene oxide is not gasified. Such conditions can be achieved by controlling the temperature in a lead pipe equipped with a jacket or by controlling the pressure by such means as a pump.

In addition, at the outlet of the aging reaction column, there may be further provided a flash distillation equipment, such as a flash tank for removing low-boiling point by-products. By flash distillation of the product resulting from the aging treatment in which the amount of the unreacted alkylene oxide dissolved in the liquid components is notably reduced, the low boiling point by-products, such as dioxane, can be effectively removed without discharging the alkylene oxide.

The resulting liquid components containing the alkylene oxide adduct after the reaction can be recirculated by leading the liquid components from the liquid outlet to the liquid inlet of the fixed bed reaction column. By the recirculation, the number of molar additions of the alkylene oxide of the resulting alkylene oxide adduct can be further increased.

Next, the reactor suitably used in the present invention will be described.

The reactor usable in the present invention includes a fixed bed reactor comprising a reaction column packed with a solid catalyst.

The fixed bed reactor usable in the present invention includes, for instance, a fixed bed reactor comprising a reaction column packed with a solid catalyst; a feed line for an alkylene oxide for feeding the alkylene oxide to the reaction column; and a feed line for an organic compound having active hydrogen for feeding the organic compound having active hydrogen to the reaction column, wherein each of the feed line for an alkylene oxide and the feed line for an organic compound having active hydrogen may be connected to the top of the reaction column. Alternatively, the feed line for an alkylene oxide may be connected to the bottom of the reaction column. Further, in the above fixed bed reactor, those further comprising a feed line for an inert gas for feeding the inert gas to the reaction column connected to the top or bottom of the reaction column are more preferably employed, and those further comprising a gas-liquid separator for efficiently separating the gas components from the liquid components at a liquid outlet of the reaction column arranged at the top or bottom of the reaction column are more preferably employed.

As to the fixed bed reactor usable in the present invention, in a case of using the fixed bed reactor in the process of the present invention, from the viewpoint of reducing the amount of the alkylene oxide dissolved in the resulting liquid components, more preferably employed ones include those further comprising an aging reaction column connected to the liquid outlet of the reaction column, or to the gas-liquid separator arranged, at the top or bottom of the reaction column.

Figure 3:
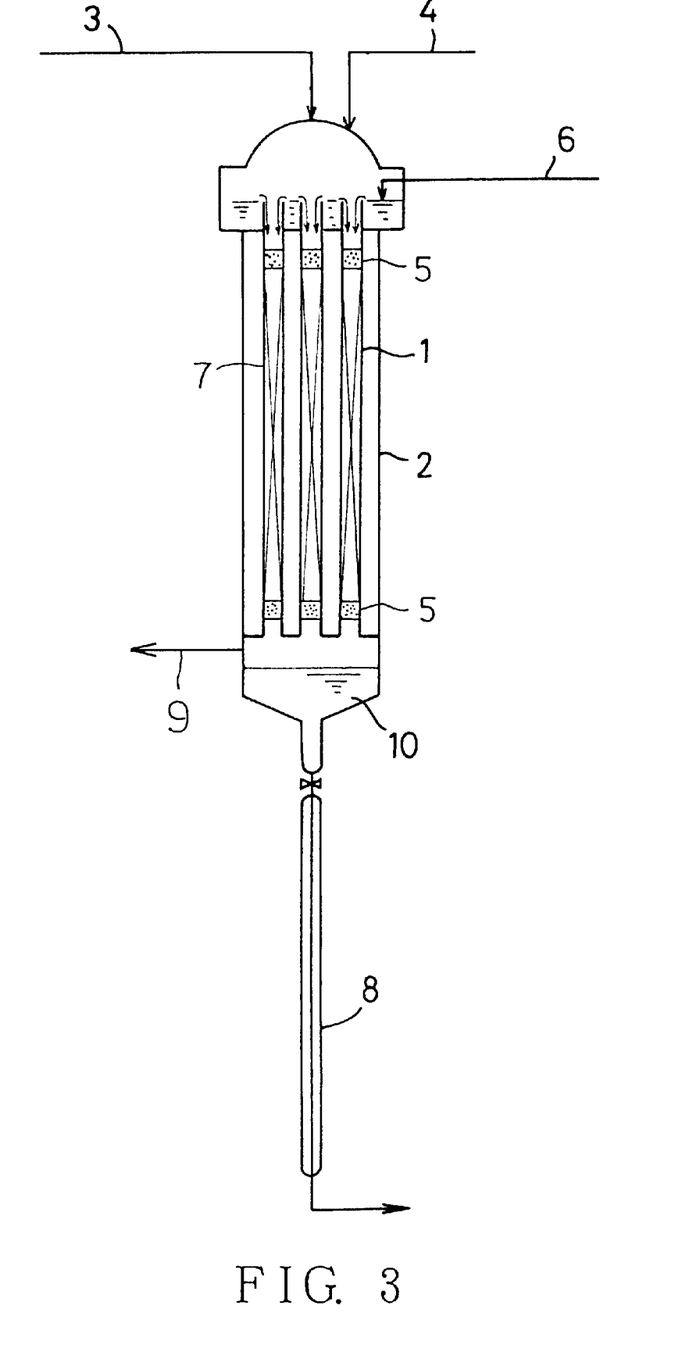
FIG. 3 is a schematic view of a fixed-bed reactor usable in one embodiment of the present invention, wherein 1 is a reaction column, 2 a jacket, 3 a feed line for an alkylene oxide, 4 a feed line for an inert gas, 5 inert particles, 6 a feed line for an organic compound having active hydrogen, 7 a solid catalyst, 8 an aging reaction column, 9 an exhaust gas line, and 10 a gas-liquid separator.

An example of the fixed bed reactor includes an apparatus as shown in FIG. 3. The apparatus shown in FIG. 3 is usually only used under conditions that the gas phase in the reaction column is a continuous phase.

Next, the present invention will be detailed referring to FIG. 3.

The organic compound having active hydrogen is fed to the top of the reaction column, a liquid inlet of the reaction column, from a feed line 6 for an organic compound having active hydrogen. In addition, the alkylene oxide is fed to the top of the reaction column from a feed line 3 for an alkylene oxide. An inert gas is fed to the top of the reaction column from a feed line 4 for an inert gas.

The liquid components fed to the top of a reaction column 1 is distributed to each reaction column by a liquid distributor arranged at the top of the reaction column. The liquid components fed to the reaction column 1 are in a downward flow reaching a solid catalyst 7 after passing through inert particles 5.

The addition reaction of the organic compound having active hydrogen with the alkylene oxide is carried out in the reaction column 1. The resulting alkylene oxide adduct mixed into the liquid components is in a downward flow.

At the bottom of the reaction column, a liquid outlet of the reaction column, there can be obtained liquid components containing an alkylene oxide adduct of an organic compound having active hydrogen, and gas components comprising an unreacted, gaseous alkylene oxide or a mixture of the unreacted, gaseous alkylene oxide and an inert gas. The liquid components are separated from the gas components at a gas-liquid separator 10, and the liquid components are discharged from the reactor, so that a desired alkylene oxide adduct can be obtained therefrom. Also, the gas components may be exhausted from an exhaust gas line 9.

In the fixed bed reactor of FIG. 3, there may be provided a jacket 2 capable of flowing a liquid in the peripheral portion of the reaction column 1. By providing the jacket 2, the temperature of the reaction column 1 can be favorably adjusted to a desired level by adjusting the temperature of the liquid flowing through the jacket 2.

In addition, from the viewpoints of effectively reacting and removing a very small amount of the alkylene oxide dissolved in the liquid components containing the alkylene oxide adduct, the fixed bed reactor may further comprise an aging reactor column 8.

EXAMPLES

The present invention will be described in further detail by means of the following working examples, without intending to limit to scope or spirit of the present invention thereto.

Example 1

A fix-bed reactor similar to that shown in FIG. 3, except that no aging reaction column was provided, was packed with a KW 2000 molding catalyst ("KW 2030," manufactured by Kyowa Chemical Industry Co., Ltd.) as a catalyst in an amount of 2 liters for each reaction column having an inner diameter of 28 mm and a length of 4 m. As to inert particles, stainless Raschig rings were used. Lauryl alcohol was fed from a feed line 6 for an organic compound having active hydrogen. By using a liquid distributor arranged at a top portion of the fixed-bed reactor, lauryl alcohol, a liquid component, was distributed, and lauryl alcohol was then allowed to flow downward through the reaction column at a flow rate of 2.4 kg/hr for each reaction column. In addition, liquid ethylene oxide was fed from a feed line 3 for an alkylene oxide at a flow rate of 7.8 kg/hr for each reaction column, and nitrogen gas was fed from a feed line 4 for an inert gas at a flow rate of 5.2 kg/hr for each reaction column.

The temperature inside the reaction column was kept at 135° C., and the pressure was kept at about 6.4 atm. Liquid components containing the resulting polyoxyethylene lauryl ether and gas components containing unreacted ethylene oxide and nitrogen gas were continuously separated in a gas-liquid separator 10. In addition, the gas components were exhausted from an exhaust gas line 9. At an inlet of the reaction column, the particle-based Reynolds number of the liquid components was 2.1, and the particle-based Reynolds number of the gas components was 1181; and at the outlet of the reaction column, particle-based Reynolds number of the liquid components was 2.4, and the particle-based Reynolds number of the gas components was 742. From the above results, it was confirmed that the flow of the liquid phase and the gas phase satisfied the wavy flow region, ethylene oxide was present in a continuous phase.

In addition, a gasification ratio of ethylene oxide was obtained from the flow rates of ethylene oxide, nitrogen gas, and lauryl alcohol, and each of their vapor pressures at the temperature and pressure conditions during reaction. The resulting gasification ratio for each of Examples is shown in Table 1.

Here, the Reynolds numbers for each component were calculated as follows:

At the inlet, $Re_l$, the particle-based Reynolds number for the liquid components, calculated by the following equation:

$$Re_l = d_s \cdot G_l / \mu_l,$$

wherein $d_s$, an equivalent catalyst diameter based on sphere,=0.38 cm;

$G_l$, a superficial mass flow rate of a liquid,=0.1147 g/cm$^2$·sec; and $\mu_l$, a viscosity of a liquid,=0.02122 g/cm·sec, was found to be 2.1. In addition, at the inlet, $Re_g$, the particle-based Reynolds number for the gas components, calculated by the following equation:

$$Re_g = d_s \cdot G_g / \mu_g,$$

wherein $d_s$, the same as defined above,=0.38 cm;

$G_g$, a superficial mass flow rate of a gas,=0.6215 g/cm²·sec; and $\mu_g$, a viscosity of a gas,=0.0002 g/cm·sec, was found to be 1181.

At the outlet, $Re_l$, the particle-based Reynolds number for the liquid components, calculated by the following equation:

$$Re_l = d_s \cdot G_l / \mu_l,$$

wherein $d_s$, the same as defined above,=0.38 cm;

$G_l$, a superficial mass flow rate of a liquid,=0.3457 g/cm²·sec; and $\mu_l$, a viscosity of a liquid,=0.05508 g/cm·sec, was found to be 2.4. In addition, at the outlet, $Re_g$, the particle-based Reynolds number for the gas components, calculated by the following equation:

$$Re_g = d_s \cdot G_g / \mu_g,$$

wherein $d_s$, the same as defined above,=0.38 cm;

$G_g$, a superficial mass flow rate of a gas,=0.3906 g/cm²·sec; and $\mu_g$, a viscosity of a gas,=0.0002 g/cm·sec, was found to be 742.

The number of molar addition of ethylene oxide of the ethylene oxide adduct of lauryl alcohol was calculated as follows. The liquid components taken out from the fixed bed were stirred for 30 minutes under the conditions of 80° C. and 30 Torr, in order to degas the unreacted ethylene oxide 7. Thereafter, the number of molar addition of ethylene oxide was calculated from the hydroxyl value of the liquid components after degassing. The results are shown in Table 1. Incidentally, APHA, the hue of the resulting ethylene oxide adduct of lauryl alcohol, was 5 or less, showing that no dramatic temperature rise took place in the reaction column.

TABLE 1

| Number of Molar Additions of EO* | Hue (APHA) | Amount of Product per Unit Volume of Reaction Column** | Gasification Ratio of EO* |
|---|---|---|---|
| Example Nos. | | | |
| 1 | 8.9 | 5 or less | 3.73 | 0.985 |
| 2 | 9.0 | 5 or less | 3.76 | 0.985 |
| 3 | 2.5 | 5 or less | 6.45 | 0.949 |
| 4 | 3.0 | 5 or less | 5.82 | 0.957 |
| 5 | 2.2 | 10 | 3.55 | 0.961 |

Remark
*Ethylene oxide.
**[kg · hr · liter]

Example 2

The same procedures as in Example 1 were carried out to prepare an ethylene oxide adduct of lauryl alcohol, except for the following conditions: Lauryl alcohol was fed from the feed line for an organic compound having active hydrogen, to allow lauryl alcohol to flow downward through the reaction column at a flow rate of 2.4 kg/hr for each reaction column. In addition, ethylene oxide, previously heated and gasified, and nitrogen gas were mixed and fed from a gas feed line 4. Each of the gas feeding rates was as follows. Ethylene oxide gas was fed at a rate of 7.8 kg/hr for each reaction column, and nitrogen gas was fed at a rate of 5.2 kg/hr for each reaction column. The results are shown in Table 1. In this case, it was confirmed that the flow of the liquid phase and the gas phase inside the reaction column satisfied the wavy flow region, ethylene oxide was present in a continuous phase. Incidentally, APHA, the hue of the resulting ethylene oxide adduct of lauryl alcohol, was 5 or less, showing that no dramatic temperature rise took place in the reaction column.

Example 3

The same procedures as in Example 1 were carried out to prepare an ethylene oxide adduct of lauryl alcohol, except for feeding lauryl alcohol from the feed line for an organic compound having active hydrogen, to allow lauryl alcohol to flow downward through the reaction column at a flow rate of 8.1 kg/hr for each reaction column. The results are shown in Table 1. In this case, it was confirmed that the flow of the liquid phase and the gas phase inside the reaction column satisfied the wavy flow region, ethylene oxide was present in a continuous phase. Incidentally, APHA, the hue of the resulting ethylene oxide adduct of lauryl alcohol, was 5 or less, showing that no dramatic temperature rise took place in the reaction column.

Example 4

The same procedures as in Example 1 were carried out to prepare an ethylene oxide adduct of lauryl alcohol, except for feeding lauryl alcohol from the feed line for an organic compound having active hydrogen, to allow lauryl alcohol to flow downward through the reaction column at a flow rate of 6.8 kg/hr for each reaction column. The results are shown in Table 1. In this case, it was confirmed that the flow of the liquid phase and the gas phase inside the reaction column satisfied the wavy flow region, ethylene oxide was present in a continuous phase. Incidentally, APHA, the hue of the resulting ethylene oxide adduct of lauryl alcohol, was 5 or less, showing that no dramatic temperature rise took place in the reaction column.

Example 5

The same procedures as in Example 1 were carried out to prepare an ethylene oxide adduct of methyl ester of a fatty acid, except for the following conditions: Methyl ester of a fatty acid having a molecular weight of 217 was fed from the feed line for an organic compound having active hydrogen, to allow methyl ester of a fatty acid to flow downward through the reaction column at a flow rate of 4.9 kg/hr for each reaction column. In addition, ethylene oxide, previously heated and gasified, and nitrogen gas were mixed and fed from a gas feed line 4. Each of the gas feeding rates was as follows. Ethylene oxide gas was fed at a rate of 5.4 kg/hr for each reaction column, and nitrogen gas was fed at a rate of 3.6 kg/hr for each reaction column. The results are shown in Table 1. In this case, it was confirmed that the flow of the liquid phase and the gas phase inside the reaction column satisfied the wavy flow region, ethylene oxide was present in a continuous phase. Incidentally, APHA, the hue of the resulting ethylene oxide adduct of the methyl ester of a fatty acid, was 10, showing that no dramatic temperature rise took place in the reaction column.

Here, the Reynolds numbers for each component were calculated as follows:

At the inlet, $Re_l$, the particle-based Reynolds number for the liquid components, calculated by the following equation:

$$Re_l = d_s \cdot G_l / \mu_l,$$

wherein $d_s$, an equivalent catalyst diameter based on sphere, 0.38 cm;

$G_l$, a superficial mass flow rate of a liquid,=0.234 g/cm²·sec; and $\mu_l$, a viscosity of a liquid,=0.010 g/cm·sec, was found to be 8.9. In addition, at the outlet, $Re_g$, the particle-based Reynolds number for the gas components, calculated by the following equation:

$$Re_g = d_s \cdot G_g / \mu_g,$$

wherein $d_s$, the same as defined above,=0.38 cm;

$G_g$, a superficial mass flow rate of a gas,=0.430 g/cm²·sec; and $\mu_g$, a viscosity of a gas,=0.0002 g/cm·sec, was found to be 817.

At the outlet, $Re_l$, the particle-based Reynolds number for the liquid components, calculated by the following equation:

$$Re_l = d_s \cdot G_l / \mu_l,$$

wherein $d_s$, the same as defined above,=0.38 cm;

$G_l$, a superficial mass flow rate of a liquid,=0.339 g/cm²·sec; and $\mu_l$, a viscosity of a liquid,=0.050 g/cm·sec, was found to be 2.6. In addition, at the inlet, $Re_g$, the particle-based Reynolds number for the gas components, calculated by the following equation:

$$Re_g = d_s \cdot G_g / \mu_g,$$

wherein $d_s$, the same as defined above,=0.38 cm;

$G_g$, a superficial mass flow rate of a gas,=0.325 g/cm²·sec; and $\mu_g$, a viscosity of a gas,0.0002 g/cm·sec, was found to be 618.

The hue in the above Examples was measured by a testing method based on Hazen unit color number according to JIS K-0071-5 using the APHA column. The production efficiency was evaluated as an amount of the resulting product per unit volume of the reaction column. Specifically, the amount of the resulting product per unit volume of the reaction column was calculated as follows. The flow rate [kg/hr] of the product was obtained from the flow rate [kg/hr] of the starting organic compounds having active hydrogen and the number of molar addition of ethylene oxide. The resultant flow rate of the product was divided by the volume (liter) of the catalyst to obtain the amount of the resulting product per unit volume of the reaction column.

It is clear from Table 1 that the ethylene oxide adducts having a large number of molar addition of ethylene oxide can be produced at a high efficiency according to the process of the present invention. In addition, each of the resulting ethylene oxide adducts has an excellent hue, showing an excellent quality.

In addition, the Reynolds numbers for each component inlet and outlet of the reaction column in each Example shown in Table 2.

TABLE 2

| Example Nos. | Particle-Based Reynolds Number of Liquid Components | | Particle-Based Reynolds Number of Gas Components | |
|---|---|---|---|---|
| | $Re_l$ at Inlet | $Re_l$ at Outlet | $Re_g$ at Inlet | $Re_g$ at Outlet |
| 1 | 2.1 | 2.4 | 1181 | 742 |
| 2 | 2.1 | 2.5 | 1181 | 716 |
| 3 | 6.9 | 7.5 | 1181 | 745 |
| 4 | 5.8 | 6.4 | 1181 | 745 |
| 5 | 8.9 | 2.6 | 817 | 618 |

According to the process of the present invention, there can be exhibited an effect of preparing an alkylene oxide adduct having an excellent hue at a high production efficiency, and with good safety and stability, without employing high-degree, pressure-tight facilities.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process for preparing an alkylene oxide adduct, comprising the steps of feeding an organic compound having active hydrogen and an alkylene oxide to a reaction column packed with a solid catalyst, and carrying out addition reaction of said organic compound having active hydrogen with an alkylene oxide in a gas-liquid fixed bed reaction, wherein the alkylene oxide is in a state of gas and the organic compound having active hydrogen is in a state of liquid.

2. The process according to claim 1, wherein the organic compound having active hydrogen and the alkylene oxide are fed to the reaction column under conditions that a gas phase therein is a continuous phase.

3. The process according to claim 1, wherein the gas phase in the reaction column comprises an inert gas and an alkylene oxide gas, or consists essentially of an alkylene oxide gas.

4. The process according to claim 1, wherein a liquid phase and the gas phase in the reaction column are cocurrent downward flow.

5. The process according to claim 1, wherein the organic compound having active hydrogen and the alkylene oxide are fed under conditions of flow of a liquid phase and a gas phase sufficient to be within a wavy flow region or a trickle flow region.

6. The process according to claim 1, further comprising an aging step.

7. The process according to claim 1, wherein a particle-based Reynolds number of a liquid in the reaction column is 1,000 or less.

8. The process according to claim 1, wherein a particle-based Reynolds number of a gas in the reaction column is 300,000 or less.

* * * * *